United States Patent
Casey et al.

(10) Patent No.: US 9,649,367 B2
(45) Date of Patent: May 16, 2017

(54) CONTRACEPTIVE VACCINES FOR MAMMALS

(71) Applicants: Irwin K. M. Liu, Kumeu (NZ); CONTRAVACCINE LIMITED, Kumeu (NZ)

(72) Inventors: Patrick J. Casey, Kumeu (NZ); Irwin K. M. Liu, Winters, CA (US)

(73) Assignee: CONTRAVACCINE LIMITED, Kumeu (NZ)

( * ) Notice: Subject to any disclaimer, the term of this patent is extended or adjusted under 35 U.S.C. 154(b) by 133 days.

(21) Appl. No.: 14/221,980

(22) Filed: Mar. 21, 2014

(65) Prior Publication Data

US 2015/0044241 A1 Feb. 12, 2015

Related U.S. Application Data

(60) Provisional application No. 61/803,967, filed on Mar. 21, 2013.

(51) Int. Cl.
| | |
|---|---|
| *C12N 15/85* | (2006.01) |
| *A61K 39/00* | (2006.01) |
| *C12N 5/071* | (2010.01) |

(52) U.S. Cl.
CPC ........ *A61K 39/0006* (2013.01); *C12N 5/0682* (2013.01); *A61K 2039/515* (2013.01)

(58) Field of Classification Search
None
See application file for complete search history.

(56) References Cited

U.S. PATENT DOCUMENTS

| 8,372,644 B2 | 2/2013 | Casey et al. |
| 2010/0329987 A1 | 12/2010 | Okabe et al. |

OTHER PUBLICATIONS

Mahi-Brown et al., chaper 4 of Birth Control Vaccines, 1995, Landes, pp. 41-61.*
Alila et al., Biol Reprod. Dec. 1984;31(5):1015-25.*
Amsterdam et al., Proc Natl Acad Sci U S A. Jun. 1980;77(6):3440-4.*
Fujiwara et al., Biol Reprod. Aug. 1995;53(2):407-17.*
Fujiwara et al., Biol Reprod. Oct. 1993;49(4):705-15.*
Dohr G., Hum Reprod. Nov. 1987;2(8):657-64.*
Bhol et al., J Dent Res. Aug. 2001;80(8):1711-5.*
Rahbar et al., J Autoimmun. May 2006;26(3):155-64. Epub Apr. 11, 2006.*
Schwimmbeck et al., J Exp Med. Jul. 1, 1987;166(1):173-81.*
Yamagiwa et al., Int J Med Sci. Jun. 8, 2014;11(9):850-6. doi: 10.7150/ijms.8633. eCollection 2014.*
Janeway et al., Immunobiology, 3$^{rd}$ edition, 1997, Garland Publishing Inc, pp. G:1, G:14, G:19, and G:21.*
Notification of Transmittal of The International Search Report and The Written Opinion of the International Searching Authority Oct. 3, 2014, International Application No. PCT/US 14/31455.
346/DEL/2001, National Institute of Immunology, "A Method for Producing an Immunocontraceptive Vaccine" Filed Mar. 23, 2001.
University of Nebraska—Lincoln, Lowell A. Miller, "Immunocontraception and Possible Application in Wildlife Damage Management", Apr. 10, 1995.
Human Reproduction, Rajesh K. Naz, et al., "Recent Advances in Contraceptive Vaccine Development: A Mini-Review", vol. 20, No. 12, pp. 3271-3283, 2005.
Supplementary European Search Report Oct. 12, 2016.
Lisa A. Harrenstien et al Effects of Porcine Zona Pellucida Mmunocontraceptives n Zoo Fields, Journal of Zoo and Wildlife Medicine, vol. 35, No. 3, Sep. 1, 2004, pp. 271-279.
McLaughlin E. A. et al "Is there a role for immunocontraception?" Molecular and Cellular Endocrinology, vol. 335, No. 1, Apr. 6, 2010, pp. 78-88.
J. F. Kirkpatrick et al "Long-term effects porcine zonae pellucidae immunocontraception on ovarian function in feral horses (Equus caballus)", Reproduction, vol. 94, No. 2, Mar. 1, 1992, pp. 437-444.

* cited by examiner

*Primary Examiner* — Michael Szperka
(74) *Attorney, Agent, or Firm* — Preti Flaherty Beliveau & Pachios LLP

(57) ABSTRACT

The invention provides a contraceptive vaccine for a female recipient of a target species of mammals including a composition of at least one of a plurality of granulosa cells and a plurality of ovarian stromal cells in combination with an adjuvant; wherein the cells are grown from a tissue sample of the cells obtained from at least one female donor of the target species which is not the same individual as the female recipient. The invention also provides a method of producing the contraceptive vaccine as well as a method of treating a female recipient with the contraceptive vaccine to prevent pregnancy.

16 Claims, 3 Drawing Sheets

CONTRACEPTIVE VACCINES FOR MAMMALS

STATEMENT REGARDING FEDERALLY SPONSORED RESEARCH OR DEVELOPMENT

Not Applicable

BACKGROUND OF THE INVENTION

The present invention broadly relates to a contraceptive vaccine for a target species of mammals, as well as a methodology for making such a contraceptive vaccine. The vaccine can be applied to a wide range of target species, including, but not limited to, cats and dogs.

Much research has gone into the examination and description of folliculogenesis, oocyte maturation, ovulation, and subsequent fertilization, in many mammalian groups. Historically, research attention focused on the description of normal fertility and how this could be harnessed to maximize reproductive outcome. However, over the past 50 years some considerable effort has gone into the development of methodologies to manipulate the reproductive cycle for the purposes of disrupting reproductive function (i.e., contraception). Such efforts have concentrated on methods to disrupt the normal reproductive cycle through the use of hormonal therapies and, more recently, methodologies to raise antibodies to block fertilization.

Current work seeking to identify contraceptive agents or vaccines has focused on generating antibodies to the zona pellucida, the outer covering of mammalian eggs. In particular, zona pellucida vaccines have been developed from pigs' eggs. These vaccines have been used in a number of animal species including for example, the horse, buffalo, elephant, bear, elk and sheep. In some of these species, namely the horse, bear, elephant and elk, this vaccine has demonstrated excellent results in preventing pregnancy, while in others it has been less successful, with results being particularly dismal in the dog and cat. It is of considerable interest as to why animal species respond so differently to the zona pellucida vaccine.

The present inventors believe that the zona pellucida vaccine does not work totally through the mechanism of blocking fertilization (as was originally hypothesized), but also has a direct role in blocking folliculogenesis, oocyte maturation, and ovulation. They believe that an immune cross reactivity of the zona pellucida antibodies to granulosa cells and/or ovarian stromal cells occurs during maturation of the ovum. The inventors contend that the zona pellucida vaccine, as currently being produced, generates a low immune cross reactivity to granulosa cells and/or ovarian stromal cells and, as such, is capable of blocking the fertilization of a few (one or two) ovulatory oocytes as well as partially interfering with folliculogenesis and ovarian function. Studies have shown that mares given two or three injections of the zona pellucida vaccine show reversible infertility, while multiple and repeated injections of the zona pellucida vaccine in mares leads to sustained antibody production and permanent infertility (Kirkpatrick, J F, Liu, I K M, Turner, J W, Jr., Naugle R, Keiper R, Long-term effects of porcine zona pellucida immunocontraception on ovarian function in feral horses (*Equus caballus*). J Rerod Fertil 1992 (94): 437-444). This leads to the conclusion that the zona pellucida vaccine has an effect on the ovaries themselves. Further support for this is the fact that oophoritis and abnormal cyclicity are consistent findings in multi-fecund species such as dogs and mice when zona pellucida is tested as a potential contraceptive vaccine. Low immunogenicity of the zona pellucida vaccine is demonstrated by its' success at blocking fertilization in low-fecund species (e.g., the horse, buffalo, sheep, elephant and bear) but less success in fully blocking ovarian function, folliculogenesis and fertilization in multi-fecund species (e.g., the dog and cat).

Accordingly, it would be desirable to develop a non-surgical sterilant or contraceptive vaccine that will be effective for most, if not all, eutherian mammals, including the cat and the dog.

BRIEF SUMMARY OF THE INVENTION

The present invention provides in one aspect a contraceptive vaccine for a female recipient of a target species of mammals. The vaccine includes a composition including at least one of a plurality of granulosa cells and a plurality of ovarian stromal cells in combination with an adjuvant; wherein the cells are grown from a tissue sample of the cells obtained from at least one female donor of the target species which is not the same individual as the female recipient.

In embodiments of the invention, the target species is selected from at least one of the order of Primata, Carnivora, Diprotodontia, Lagomorpha, and Rodentia. In one such embodiment, the target species selected from the order of Carnivora is selected from of at least one of the genus *Canis* and the genus *Felis*. In a second such embodiment, the target species selected from the order of Diprotodontia is selected from the family Didelphidae. In a third such embodiment, the target species selected from the order of Diprotodontia is selected from the family Leporidae. In a fourth such embodiment, the target species selected from the order of Rodentia is selected from the genus *Rattus*. In a fifth such embodiment, the target species selected from the order of Primata is the species of *Homo sapiens*.

In another embodiment of the invention, the adjuvant is selected from the group consisting of aluminum salt based adjuvants, yeast based adjuvants, micro sphere based adjuvants, freunds based adjuvants, oil based adjuvants, virosome based adjuvants and micro-particle based adjuvants. In still another embodiment, the adjuvant is selected on the basis of the target species and a method of administration to the female recipient.

In another aspect, the invention provides a method of producing a contraceptive vaccine for a recipient female of a target species of mammals. The method includes the steps of obtaining a tissue sample including at least one of a plurality of granulosa cells and a plurality of ovarian stromal cells from at least one female donor of the target species which (who) is not the same individual as the female recipient; growing the cells from the tissue sample to produce a supply of grown cells; harvesting a portion of the grown cells; and combining the portion of the harvested grown cells with an adjuvant to form the contraceptive vaccine for the recipient female.

In one embodiment, the step of obtaining the tissue sample includes using at least one of a surgical excision technique and a biopsy technique to extract the tissue sample from at least one ovary of the female donor. In another embodiment, the step of harvesting the portion of the grown cells comprises digesting the portion with Trypsin and Ethylenediaminetetraacetic acid (EDTA).

In yet another aspect, the invention provides a method of treating at least one female recipient of a target species of mammals to prevent pregnancy. The method includes the steps of introducing a contraceptive vaccine into the female recipient of the target species using a method of administration; wherein the contraceptive vaccine comprises a composition of at least one of a plurality of granulosa cells and a plurality of ovarian stroma cells in combination with an adjuvant selected on the basis of the target species and the method of administration; and wherein the cells are grown from a tissue sample of the cells obtained from at least one female donor of the target species which is a different individual from the female recipient. In one embodiment, the method includes the method of administration includes at least one of oral administration, nasal administration, intra-ocular administration, intra-vaginal administration, subcutaneous injection, and intramuscular injection.

BRIEF DESCRIPTION OF THE SEVERAL VIEWS OF THE DRAWINGS

Further features of the present invention will become apparent from the following description of embodiments thereof, given by way of example only, with reference to the accompanying drawings, in which.

DETAILED DESCRIPTION OF THE INVENTION

This application claims priority to the previously filed U.S. Provisional Application No. 61/803,967 filed on Mar. 21, 2013 and hereby incorporates by reference that entire disclosure of Provisional Application No. 61/803,967.

Figure 1:
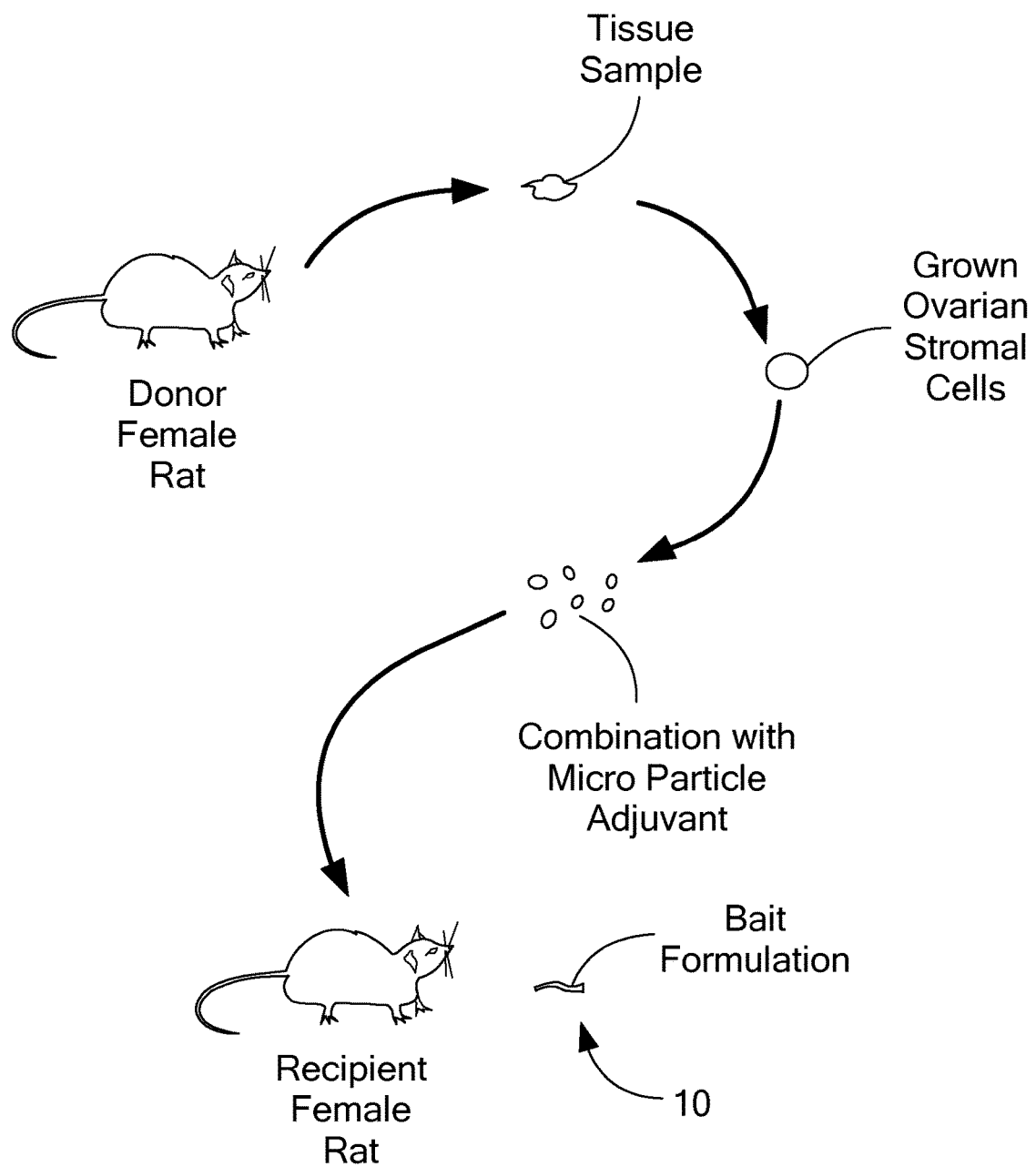
FIG. 1 illustrates a composition according to an embodiment of the invention.

The present invention provides in one aspect a contraceptive vaccine for a female recipient of a target species of mammals. The vaccine includes a composition of at least one of granulosa cells and/or ovarian stromal cells in combination with an adjuvant. The granulosa cells and the ovarian stromal cells are grown from a tissue sample obtained from a female donor of the target species which is not the same individual as the female recipient of the target species. The vaccine composition is a non-surgical sterilant including an adjuvant selected for a high but safe immunogenicity in the female recipient. It has been surprisingly found that the administration of a composition including the combination of either granulsa cells and/or ovarian stroma cells grown in a laboratory and combined with an adjuvant selected for the target species and the method of administration to the female recipient stimulates the recipient female's immune system against its own reproductive tract including the various organs, tissues, vessels and/or tubes which make up the recipient female's reproductive system. The immune system of the female recipient recognizes the vaccine composition as foreign and rejects the possibility of pregnancy as a result of administration of the vaccine. FIG. 1 illustrates one embodiment of this aspect of the invention wherein the vaccine composition 10 includes ovarian stromal cells grown from a tissue sample obtained from a female donor rat in combination a micro-particle adjuvant for oral administration via rat bait to a female rat recipient which is a different individual from the female donor rat.

The vaccine is effective at preventing pregnancy in the most fecund of species. The vaccine is capable of preventing pregnancy in the female recipients of the target species for at least one year, and preferably for at least three years, and more preferably for at least five years, and most preferably for life. At least one, and preferably one to ten, and more preferably one to five, and most preferably one to three repeated vaccinations are needed to achieve sterilization.

The number of vaccinations necessary for effective sterilization as well as the time intervals between vaccinations are selected on the basis of the target species and the method of administration selected for the vaccines according to methods employed by those of ordinary skill in the art.

The target species can include all mammals. Preferably, the target species includes mammals of the orders of Primata, Carnivora, Diprotodontia, Lagomorpha, and Rodentia. Mammals of the order Primata more preferably include the target species of *Homo sapiens* (humans) where sterilization may be desirable such as, for example, when a female suffers from polycystic ovarian disease (POD). Mammals of the order Carnivora more preferably include target species selected from the genus *Canis* (dogs) and the genus *Felis* (cats). Mammals of the order Diprotodontia more preferably include target species elected from the family Didelphidae such as, for example, opossums. Mammals of the order Lagomorpha more preferably include target species selected from the family Leporidae such as, for example, rabbits. Mammals of the order Rodentia more preferably include target species selected from the genus *Rattus* (rats).

Figure 2:
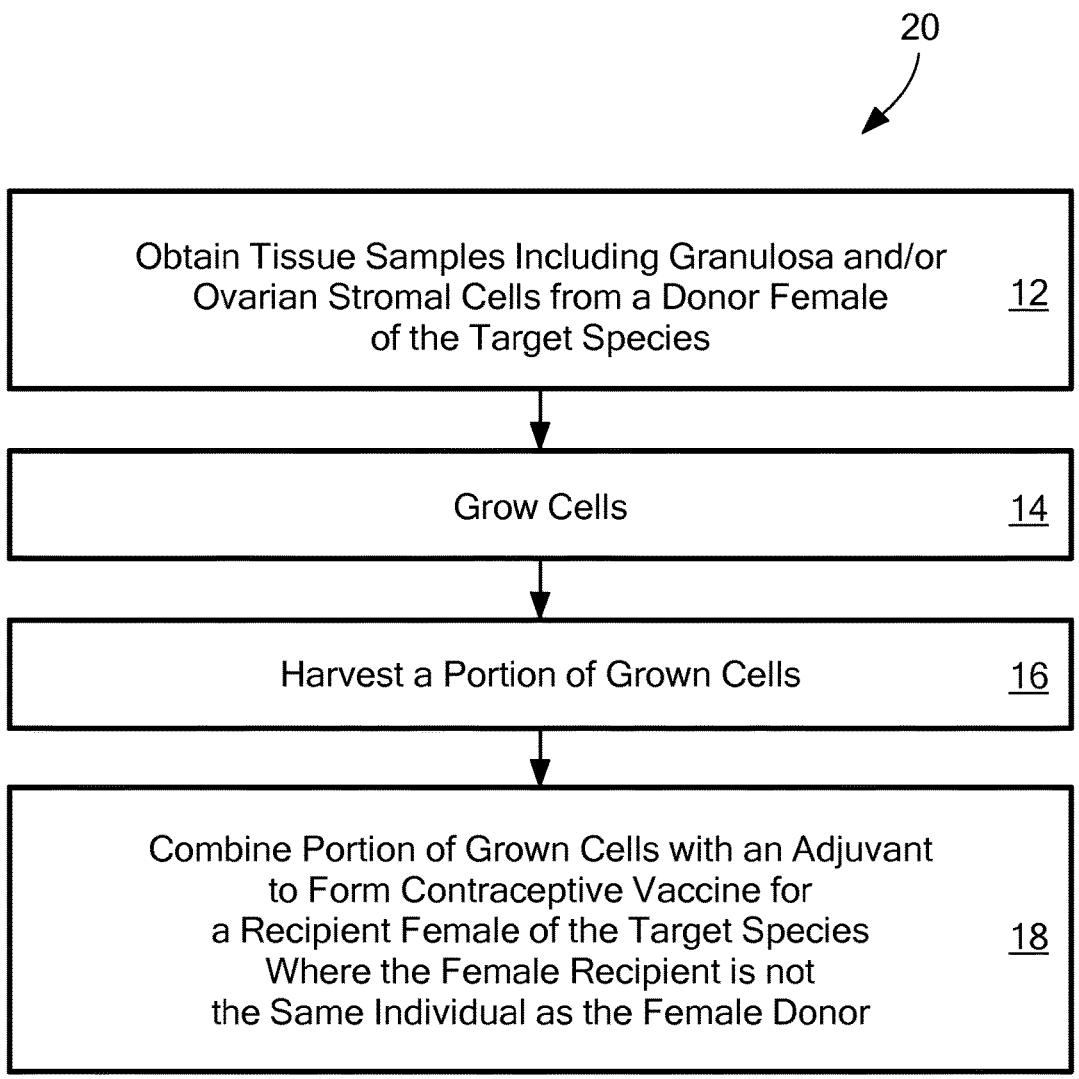
FIG. 2 illustrates steps of a method of producing a contraceptive vaccine for a target species of mammals according to an embodiment of the invention.

FIG. 2 provides an illustrated embodiment showing the steps of a method 20 for producing the contraceptive vaccine of the present invention. The amount of tissue sample obtained for growing the cells illustrated in step 12 is based on minimizing tissue damage during tissue retrieval while obtaining the sufficient amount of tissue to grow the supply of cells needed for the related vaccine. Similarly, the manner in which the tissue sample is obtained is selected on a similar basis. In one embodiment, a tissue sample of granulosa cells and/or ovarian stromal cells is obtained from the ovary of the donor female using either a surgical excision technique or a biopsy technique known to those of ordinary skill in the art.

The cells are grown as illustrated in step 16 of FIG. 2 using cell cultures for putting the granulosa cells and/or ovarian stromal cells into a dividing (mitotic) state which leads to vast cell multiplication and production.

The harvested tissue sample is transported to a laboratory preferably at ambient temperatures, such as, for example, 12° C. to 30° C., and preferably 20° C. to 24° C., and more preferably at 22° C. for in vitro growth of cells. The sample should be transported in culture media that contains protein (for example Fetal Calf serum 5-19%). The obtained tissue sample is placed in a unique culture system including, for example, a culture vessel such as a culture flask. In one embodiment, the tissue sample is broken down into tissue fragments to enhance cellular growth, as shown in as shown in step 22 of FIG. 3. Tissue fragmentation is accomplished with any suitable technique known to those of ordinary skill in the art, including but not limited to dissection, chemical digestion, and physical digestion. In one embodiment, a proteolytic enzyme such as, for example, Trypsin, in conjunction with a calcium stabilizing agent such as, for example, EDTA, is used to break down junctions between tissues to form tissue fragments.

Media is supplied to the culture system for moisture and nutrients. In a preferred embodiment, media is initially kept separate from the tissue fragments so that the tissue fragments are kept moist but deprived of physical contact with the media during a nutrient deprivation phase, as shown in step 24 of FIG. 3. The moisture induces the tissue fragments to adhere, attach and/or "stick" to the culture vessel which is necessary for the cells to grow and divide. The tissue fragments undergo a period or phase of nutrient deprivation because the fragments are initially kept isolated from the media. The nutrient deprivation phase can last from 12 to 76 hours, and preferably from 24 hours to 60 hours, and more preferably from 36 hours to 48 hours, and most preferably for approximately 48 hours until the cells slow down into the desired stressed state.

In one embodiment, the tissue fragments are placed in a modified "hanging drop" culture system wherein the fragments are placed into a culture flask with only enough media to keep the tissue fragments moist, but not suspended. The flask is then flipped over (or partially tipped) and a small amount of media is added to the bottom to keep the tissue fragments humidified. With the flask inverted, the fragments are stressed by gravity but tend to remain in contact with the flask surface due to the moisture from the media.

Figure 3:
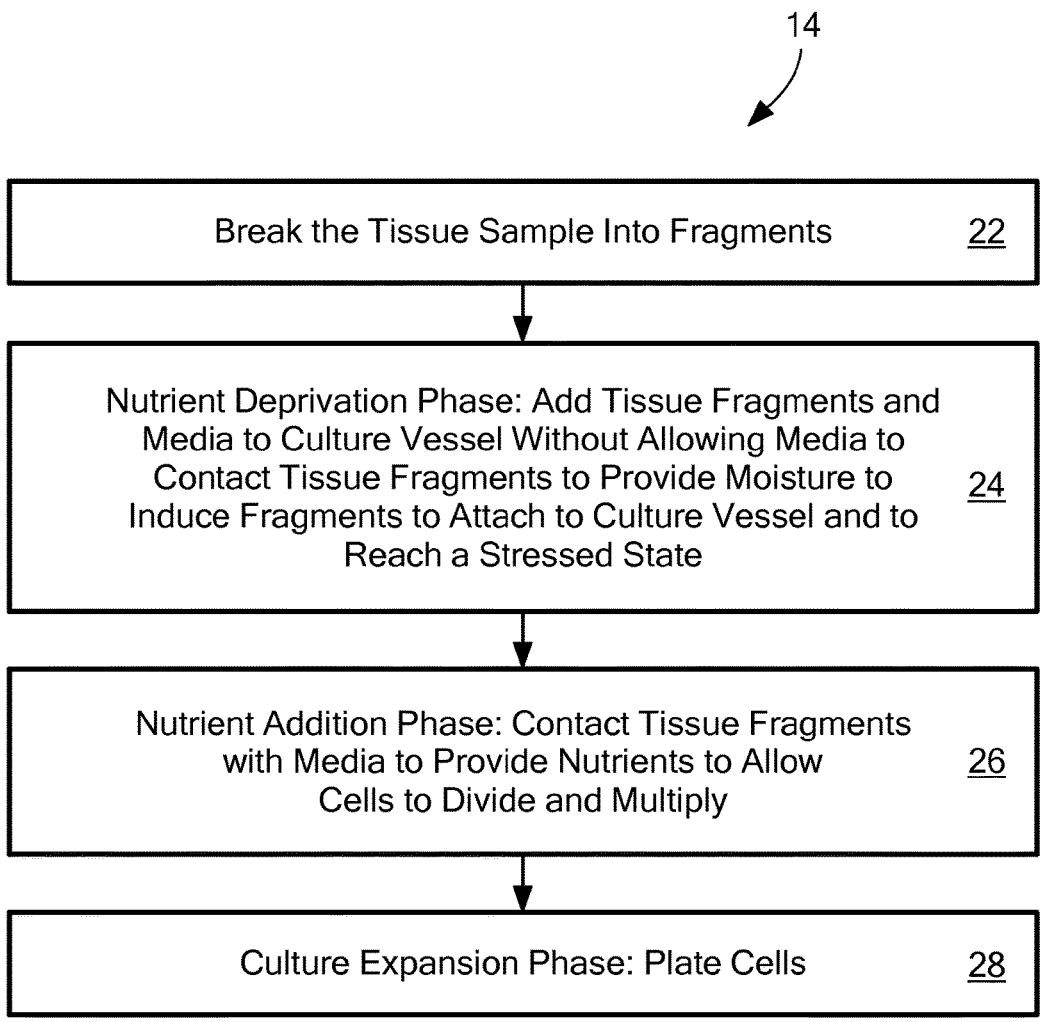
FIG. 3 illustrates the step of growing cells for the contraceptive vaccine according to an embodiment of the invention.

Prior to death of the cells, the tissue sample including tissue fragments are physically contacted with media during a nutrient addition phase to provide nutrients to the cells, as shown in step 26 of FIG. 3. Media is physically contacted with and/or added to the tissue fragments through methods known to those of ordinary skill in the art. The stressed cells respond to the introduction of nutrients in the media by initially entering into a pre-mitotic state and eventually entering a mitotic state and dividing. The media is refreshed at periods known to those of ordinary skill in the art, at for example, 1 to 4 day intervals and more preferably and 2-3 day intervals. The conditions for cellular growth including, for example, the type and amount of media added to the culture system as well as the length of the nutrient addition phase depend upon the initial amount of tissue sample, the desired amount of cell growth given the type of cells being grown (granulosa or ovarian stomal cells) and the target species. The pre-mitotic state can last generally from 8-10 days. The mitotic state can last generally from 32 to 48 hours.

The culture system is maintained until a predetermined amount of cells is grown after a preselected period of time. Contact between normal non-cancerous cells inhibits growth, however. When the cells are 60-90% confluent, and preferably 70-80% confluent, the cells are pulled apart, re-suspended, and plated in another culture system to maintain cell growth in the mitotic state. This step is shown as the culture expansion phase in step 28 of FIG. 3.

After the appropriate number of cell division cycles have been completed, a sample including a suspension of grown cells is harvested. Preferably, the grown cells are harvested from the culture system using a Trypsin/EDTA incubation technique and washed using phosphate buffered saline. Typically the cells which have been pulled apart in the digestion process remain apart for up to 48 hours. The granulosa cells and/or ovarian stromal cells can then be harvested using any suitable technique known to those of ordinary skill in the art, such as a Trypsin/EDTA incubation technique. Millions of granulosa cells and/or ovarian stromal cells can be produced using these methodologies.

The sample including the suspension of grown cells is centrifuged and the centrifuged grown cells are combined at ambient temperatures with the adjuvant to produce composition forming the vaccine, as shown in step 18 of FIG. 2. The adjuvant is selected based upon immunogenicity of the adjuvant in the target species and the route of administration. The adjuvant is selected to heighten the immune system response so that the recipient's immune system recognizes a foreign protein and is stimulated in a localized rather than generalized area while simultaneously avoiding the vaccine causing safety concerns in the recipient. Various adjuvants could be used in the present invention. Possible adjuvants include, but are not limited to, aluminum salt based adjuvants, yeast based adjuvants, micro sphere based adjuvants, freunds based adjuvants, oil based adjuvants, virosome based adjuvants and micro-particle based adjuvants. For non-limiting examples, aluminum salt based adjuvants can be used in humans, cats and dogs; yeast based adjuvants can be used in horses and possibly humans; and freunds based adjuvants can be used in many species, such as horses. Adjuvants for the vaccines formulated for oral administration via bait for mammals such as, for example, mammals of the orders of Diprotodontia, Lagomorpha, and Rodentia, are selected for their ability to withstand intestinal degradation as well as their ability to pass across the intestinal barrier into the blood.

The contraceptive vaccine can be preserved with formalin or other preservatives according to methods known to those of ordinary skill in the art for up to two years, and preferably for up to 18 months, and more preferably for up to 12 months, and most preferably for up to 6 months. Alternatively, the vaccine can be freeze dried according to methods known to those of ordinary skill in the art. The freeze dried vaccine can be stored long term at 4-5° C. temp for long term storage) for up to six months, and preferably for up to one year, and preferably for up to three years, and most preferably for up to 5 years, as long as the protein is protected and maintains its immunogenicity which is evaluated upon application.

The vaccine can be applied or administered using techniques for the administration of proteins known to one of ordinary skill in the art including, for non-limiting examples, oral administration, nasal administration, intra-ocular administration, intra-vaginal administration, subcutaneous injection, and intramuscular injection.

The number of grown granulosa cells and/or ovarian stromal cells needed to produce a vaccine which can prevent pregnancy in the target species depends upon the target species and the administration or application method or technique used to introduce the vaccine into the recipient female. The vaccine can include numbers of cells which are far greater (by orders of magnitude) than the numbers of cells initially obtained in the tissue sample of the target species. It is possible to use anywhere from one thousand cells to 100 million cells in a vaccine including 0.5 to 1 ml of adjuvant.

The foregoing examples and detailed description are not to be deemed limiting of the invention which is defined by the following claims. The invention is understood to encompass such obvious modifications thereof as would be apparent to those of ordinary skill in the art.

What is claimed is:

1. A contraceptive vaccine for a female recipient of a target species of mammals comprising:
a composition including at least one of a plurality of granulosa cells and a plurality of ovarian stromal cells in combination with an adjuvant;
wherein the cells are grown from a tissue sample of the cells obtained from at least one female donor of the target species which is not the same individual as the female recipient; and
wherein the target species is not Homo sapiens.

2. The contraceptive vaccine of claim 1, wherein the target species is selected from at least one of the order of Carnivora, Diprotodontia, Lagomorpha, and Rodentia.

3. The contraceptive vaccine of claim 2, wherein the target species selected from the order of Carnivora is selected from of at least one of the genus *Canis* and the genus *Felis*.

4. The contraceptive vaccine of claim 2, wherein the target species selected from the order of Diprotodontia is selected from the family Didelphidae.

5. The contraceptive vaccine of claim 2, wherein the target species is selected from the order of Lagomorpha is selected from the family Leporidae.

6. The contraceptive vaccine of claim 2, wherein the target species is selected from the order of Rodentia is selected from the genus *Rattus*.

7. The contraceptive vaccine of claim 1, wherein the adjuvant is selected from the group consisting of aluminum salt based adjuvants, yeast based adjuvants, micro sphere based adjuvants, freunds based adjuvants, oil based adjuvants, virosome based adjuvants and microparticle based adjuvants.

8. The contraceptive vaccine of claim 1, wherein the adjuvant is selected on the basis of the target species and a method of administration to the female recipient.

9. A method of producing a contraceptive vaccine for a recipient female of a target species of mammals, the method comprising:
  obtaining a tissue sample including at least one of a plurality of granulosa cells and a plurality of ovarian stromal cells from at least one female donor of the target species which is not the same individual as the female recipient;
  growing the cells from the tissue sample to produce a supply of grown cells;
  harvesting a portion of the grown cells; and
  combining the portion of the harvested grown cells with an adjuvant to form the contraceptive vaccine for the recipient female recipient;
  wherein the target species is not Homo sapiens.

10. The method of claim 9, wherein target species is selected from at least one of the order of Carnivora, Diprotodontia, Lagomorpha, and Rodentia.

11. The method of claim 9 wherein the step of obtaining the tissue sample comprises using at least one of a surgical excision technique and a biopsy technique to extract the tissue sample from at least one ovary of the female donor.

12. The method of claim 9 wherein the step of harvesting the portion of the grown cells comprises digesting the portion with Trypsin and EDTA.

13. A method of treating at least one female recipient of a target species of mammals to prevent pregnancy comprising:
  introducing a contraceptive vaccine into the female recipient of the target species using a method of administration;
  wherein the contraceptive vaccine comprises a composition of at least one of a plurality of granulosa cells and a plurality of ovarian cells in combination with an adjuvant selected on the basis of the target species and the method of administration to the female recipient;
  wherein the cells are grown from a tissue sample of the cells obtained from at least one female donor of the target species which is a different individual from the female recipient; and
  wherein the target species is not *Homo sapiens*.

14. The method of claim 13, wherein the target species is selected from at least one of the order of Carnivora, Diprotodontia, Lagomorpha, and Rodentia.

15. The method of claim 13, wherein the method of administration includes at least one of oral administration, nasal administration, intra-ocular administration, intra-vaginal administration, subcutaneous injection, and intramuscular injection.

16. The contraceptive vaccine of claim 1, wherein the contraceptive vaccine is in an effective amount for prevention of pregnancy in the female recipient.

* * * * *